US009655585B2

(12) United States Patent
Watanabe et al.

(10) Patent No.: US 9,655,585 B2
(45) Date of Patent: May 23, 2017

(54) X-RAY DIAGNOSTIC APPARATUS AND DOSE DISTRIBUTION GENERATION METHOD

(71) Applicant: Toshiba Medical Systems Corporation, Otawara-shi (JP)

(72) Inventors: Yuichiro Watanabe, Yaita (JP); Takuya Sakaguchi, Utsunomiya (JP); Masanori Matsumoto, Nasushiobara (JP)

(73) Assignee: Toshiba Medical Systems Corporation, Otawara-shi (JP)

( * ) Notice: Subject to any disclaimer, the term of this patent is extended or adjusted under 35 U.S.C. 154(b) by 184 days.

(21) Appl. No.: 14/496,206

(22) Filed: Sep. 25, 2014

(65) Prior Publication Data

US 2015/0139393 A1 May 21, 2015

(30) Foreign Application Priority Data

Nov. 15, 2013 (JP) ................................ 2013-237440

(51) Int. Cl.

*A61B 6/00* (2006.01)
*G06T 11/60* (2006.01)
*G09G 5/377* (2006.01)

(52) U.S. Cl.

CPC ............ *A61B 6/542* (2013.01); *A61B 6/4014* (2013.01); *A61B 6/4441* (2013.01); *A61B 6/463* (2013.01); *G06T 11/60* (2013.01); *G09G 5/377* (2013.01); *G09G 2340/12* (2013.01); *G09G 2380/08* (2013.01)

(58) Field of Classification Search

CPC .. G01N 23/04; G01N 2223/408; A61B 6/542; A61B 6/4233; A61B 6/461; A61B 6/54; A61B 6/022; A61B 6/4452; G06T 2207/10116

See application file for complete search history.

(56) References Cited

U.S. PATENT DOCUMENTS

| | | | | |
|---|---|---|---|---|
| 6,307,914 B1 * | 10/2001 | Kunieda | A61B 6/12 | 378/65 |
| 7,656,998 B2 * | 2/2010 | Main | A61N 5/1049 | 378/19 |
| 2012/0069968 A1 * | 3/2012 | Core | A61N 5/1049 | 378/206 |

FOREIGN PATENT DOCUMENTS

| | | |
|---|---|---|
| JP | 4537506 | 9/2010 |

* cited by examiner

*Primary Examiner* — Hoon Song

(74) *Attorney, Agent, or Firm* — Oblon, McClelland, Maier & Neustadt, L.L.P.

(57) ABSTRACT

An X-ray diagnostic apparatus includes a first support mechanism supporting a first X-ray tube which irradiates an object with first X-rays along a first direction, a second support mechanism supporting a second X-ray tube which irradiates the object with second X-rays along a second direction different from the first direction, a dose distribution generation unit generates a first and second dose distribution corresponding to the first and second X-rays respectively, a specifying unit specifying position states of the first and second support mechanism and operation states of the first and second X-ray tube, a display unit simultaneously displaying, with at least two different viewpoints in accordance with the position states and the operation states, a model on which the first and second dose distribution are superimposed.

14 Claims, 11 Drawing Sheets

X-ray diagnostic apparatus

29 Image generation unit
19
7 First X-ray detector
27 Driving unit
Input unit ~37
Display unit ~41
Specifying unit ~39
Control unit ~43
Z X Y
21 23 P 24
15~ ~17
25 13 11
First X-ray tube 9
5
33~ Storage unit
35~ Dose distribution generation unit
3 High voltage generation unit
Interface unit
31
Network
~1

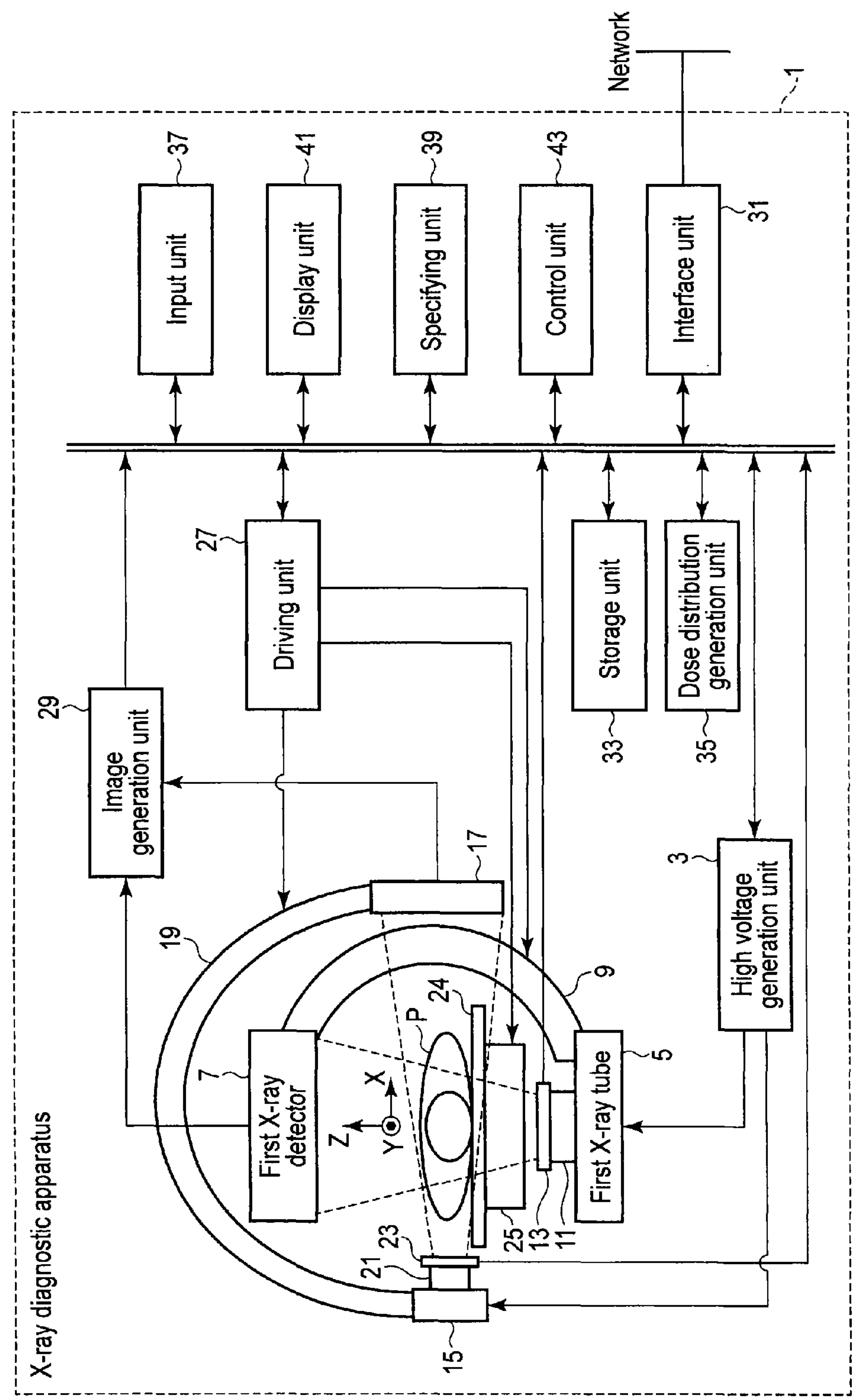
F I G. 2

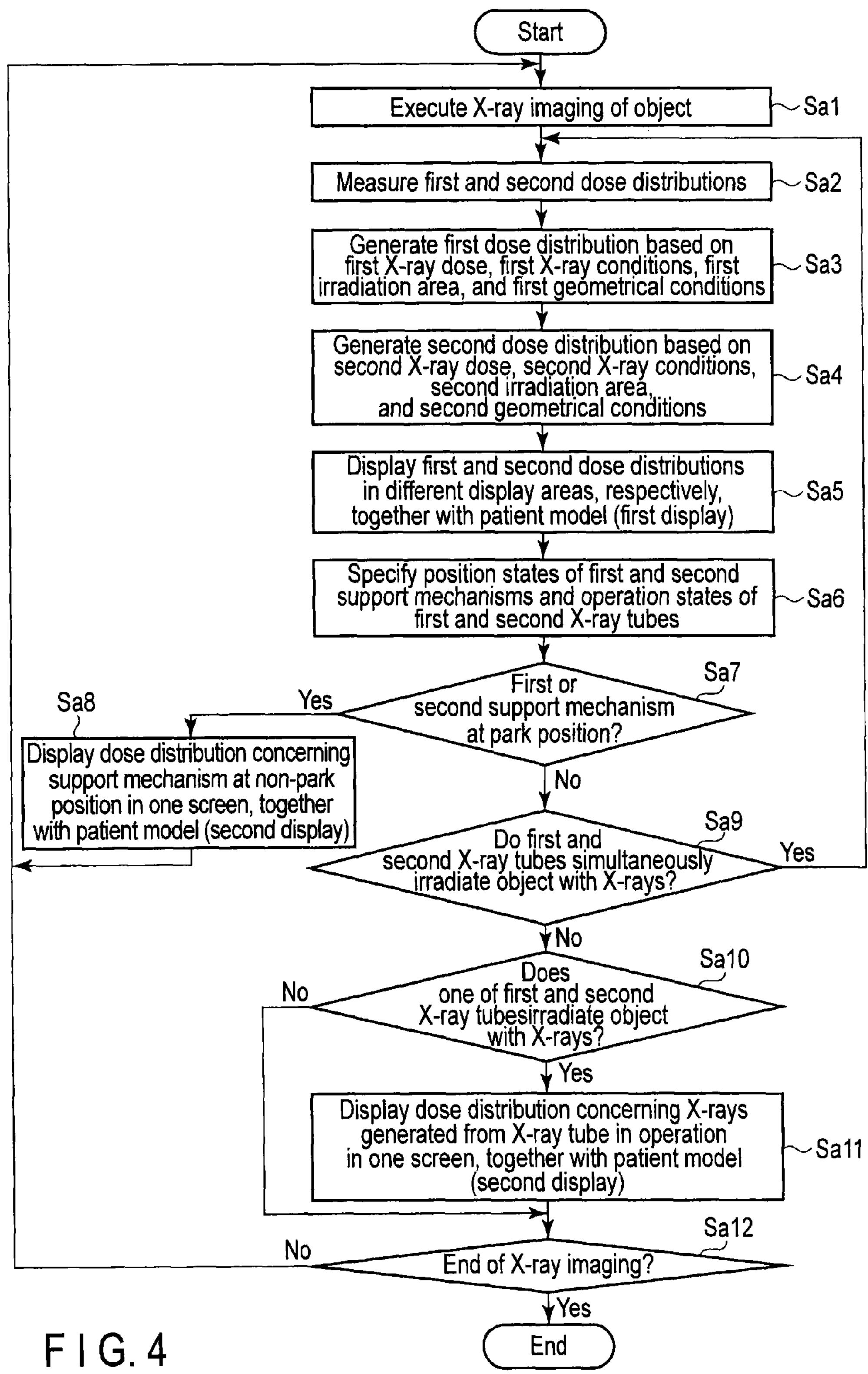
F I G. 4

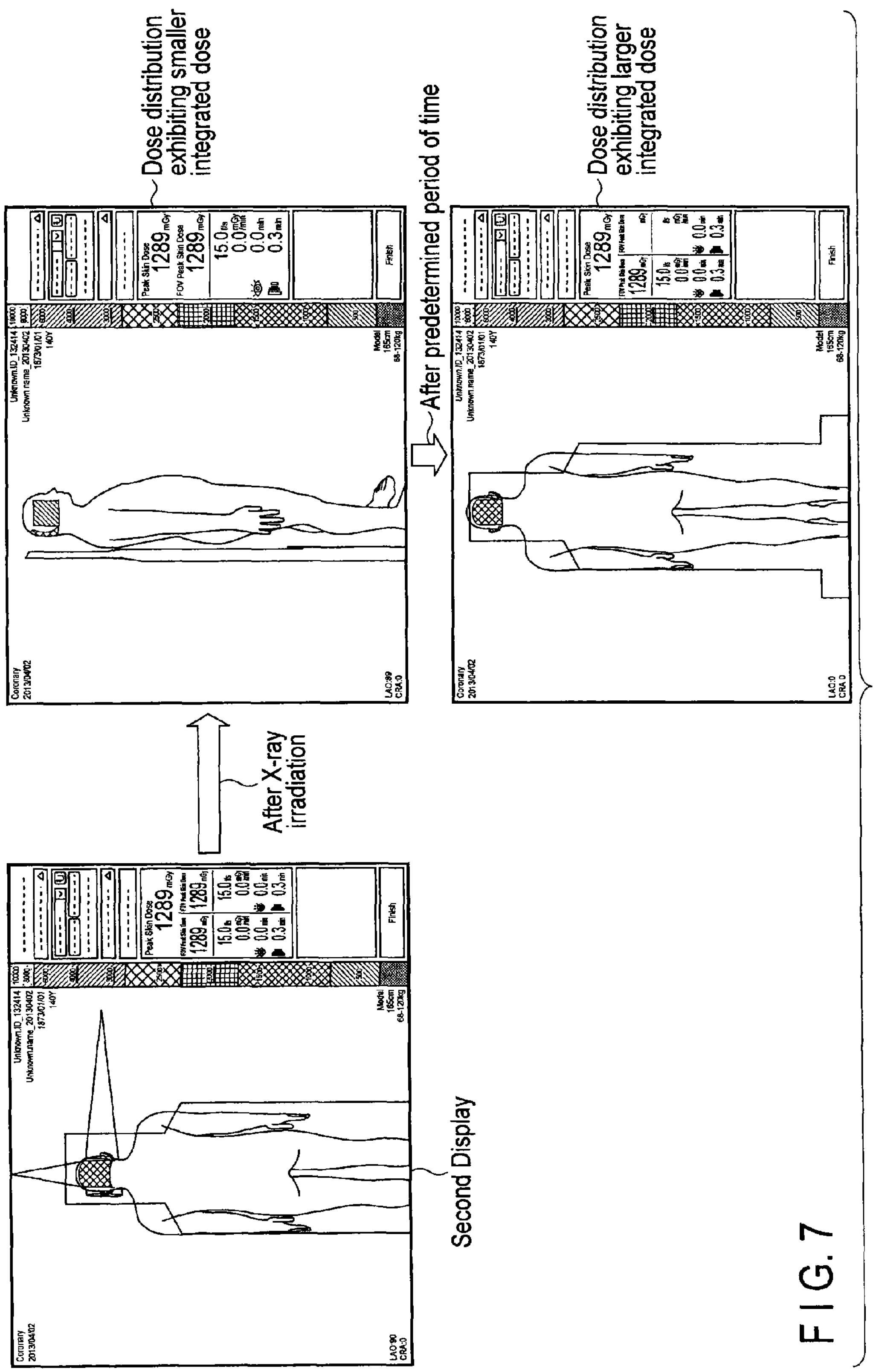
F I G. 7

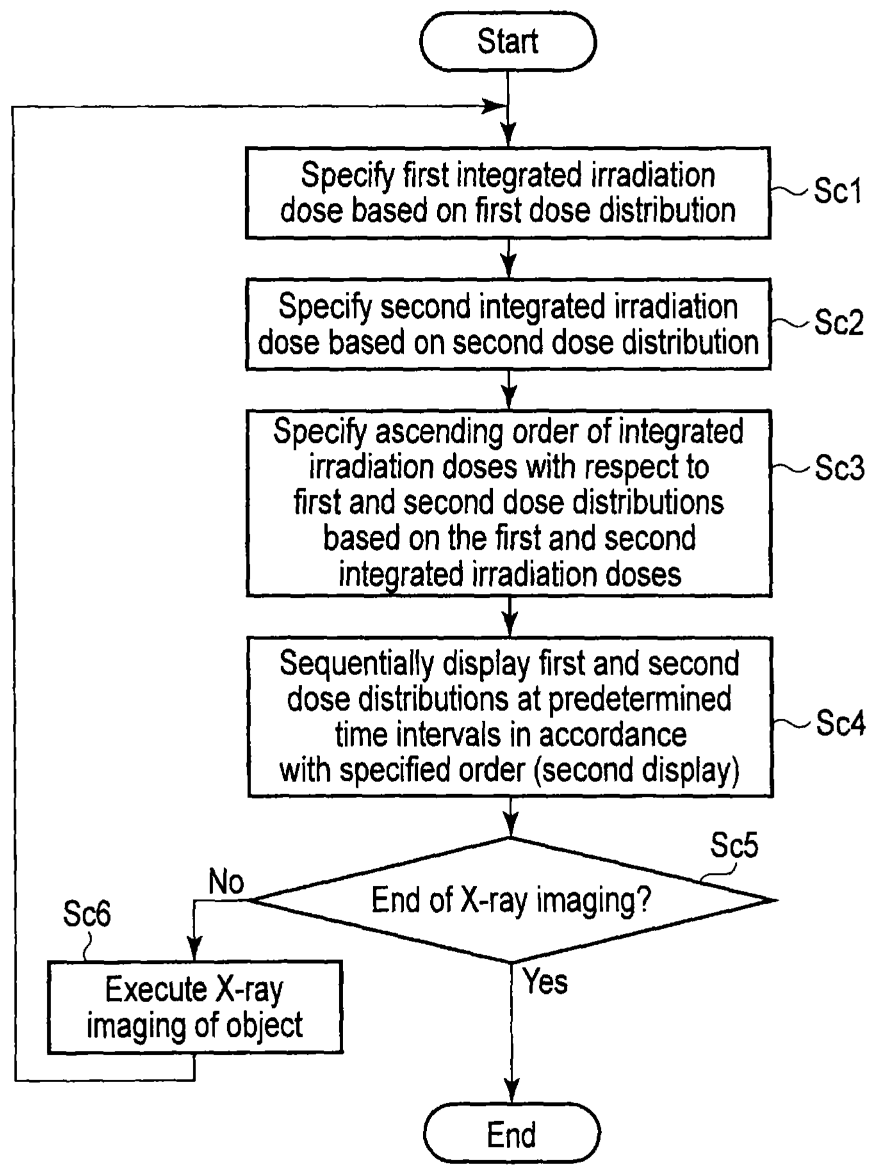
F I G. 8

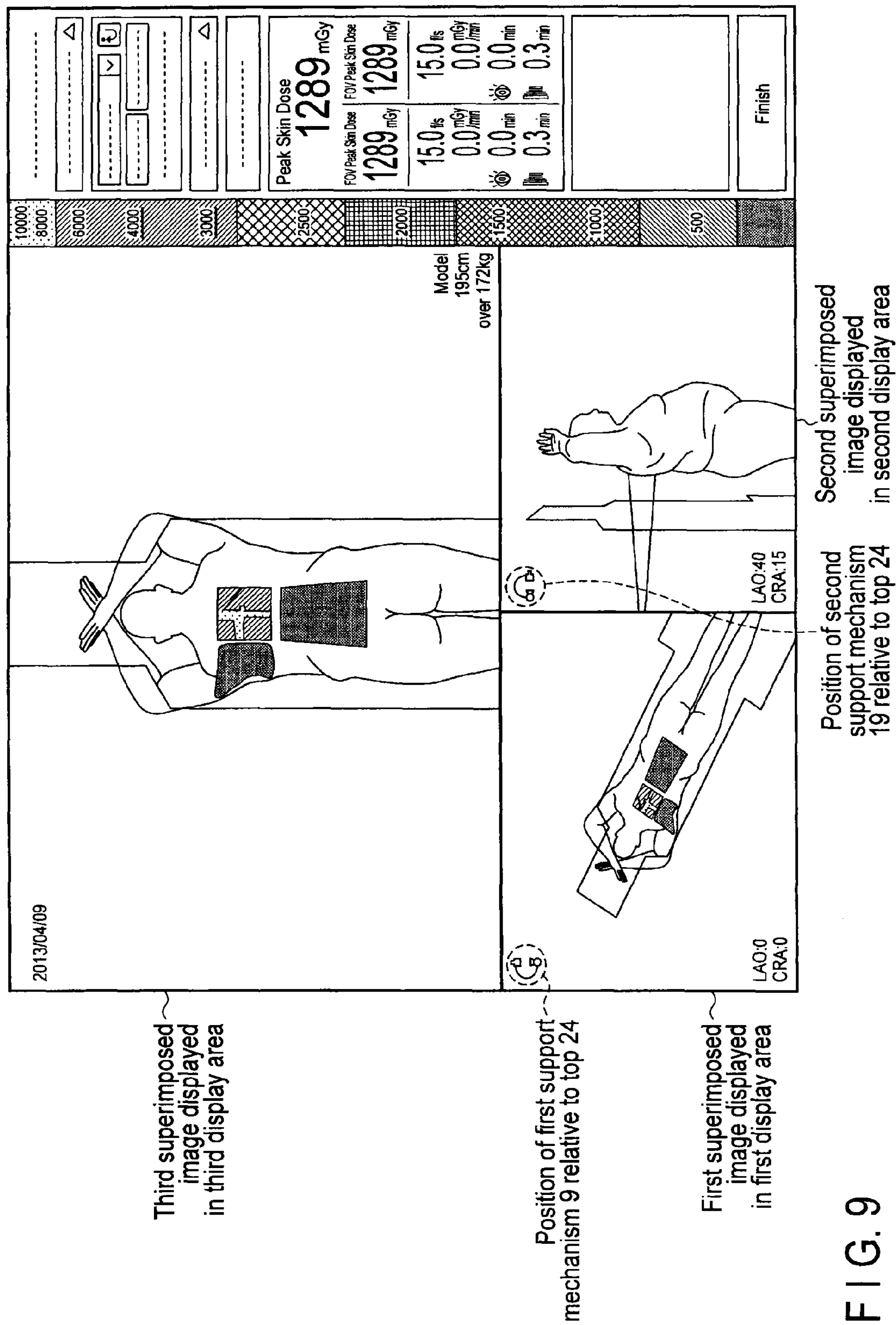
F I G. 9

Example of dose distribution

X-RAY DIAGNOSTIC APPARATUS AND DOSE DISTRIBUTION GENERATION METHOD

CROSS-REFERENCE TO RELATED APPLICATIONS

This application is based upon and claims the benefit of priority from the prior Japanese Patent Application No. 2013-237440, filed Nov. 15, 2013, the entire contents of which are incorporated herein by reference.

FIELD

Embodiments described herein relate generally to an X-ray diagnostic apparatus and a dose distribution generation method.

BACKGROUND

In IVR (Interventional Radiology) using a medical image diagnostic apparatus such as an X-ray diagnostic apparatus, there is available a function (to be referred to as an exposure distribution display function hereinafter) of displaying the distribution of exposure (to be referred to as an exposure distribution hereinafter) on an object. In the exposure distribution display function, the dose distribution of an object is displayed on one screen, as shown in each of a and b in FIG. 11.

The current exposure distribution display function, however, has a problem that it is only possible to check the exposure distribution of an object viewed from one direction. For example, an X-ray diagnostic apparatus having a single plane system has one irradiation field, and hence has no problem concerning the exposure distribution display function. However, an X-ray diagnostic apparatus having a biplane system has two irradiation fields, and hence has a problem that the operator cannot simultaneously check two irradiation fields.

BRIEF DESCRIPTION OF THE DRAWINGS

FIG. 2 is a block diagram showing the arrangement of the X-ray diagnostic apparatus according to this embodiment;

FIG. 4 is a flowchart showing an example of a procedure for dose distribution switching processing according to this embodiment;

FIG. 7 shows an example of switching between dose distributions to be displayed as the second display based on a specified order according to the second modification of this embodiment;

FIG. 8 is a flowchart showing an example of a procedure for dose distribution switching function associated with the dose distribution switching function according to the second modification of this embodiment;

FIG. 9 is a view showing an example of how the first to third superimposed images are respectively displayed in the first to third display areas according to the third modification of this embodiment;

DETAILED DESCRIPTION

Figure 1:
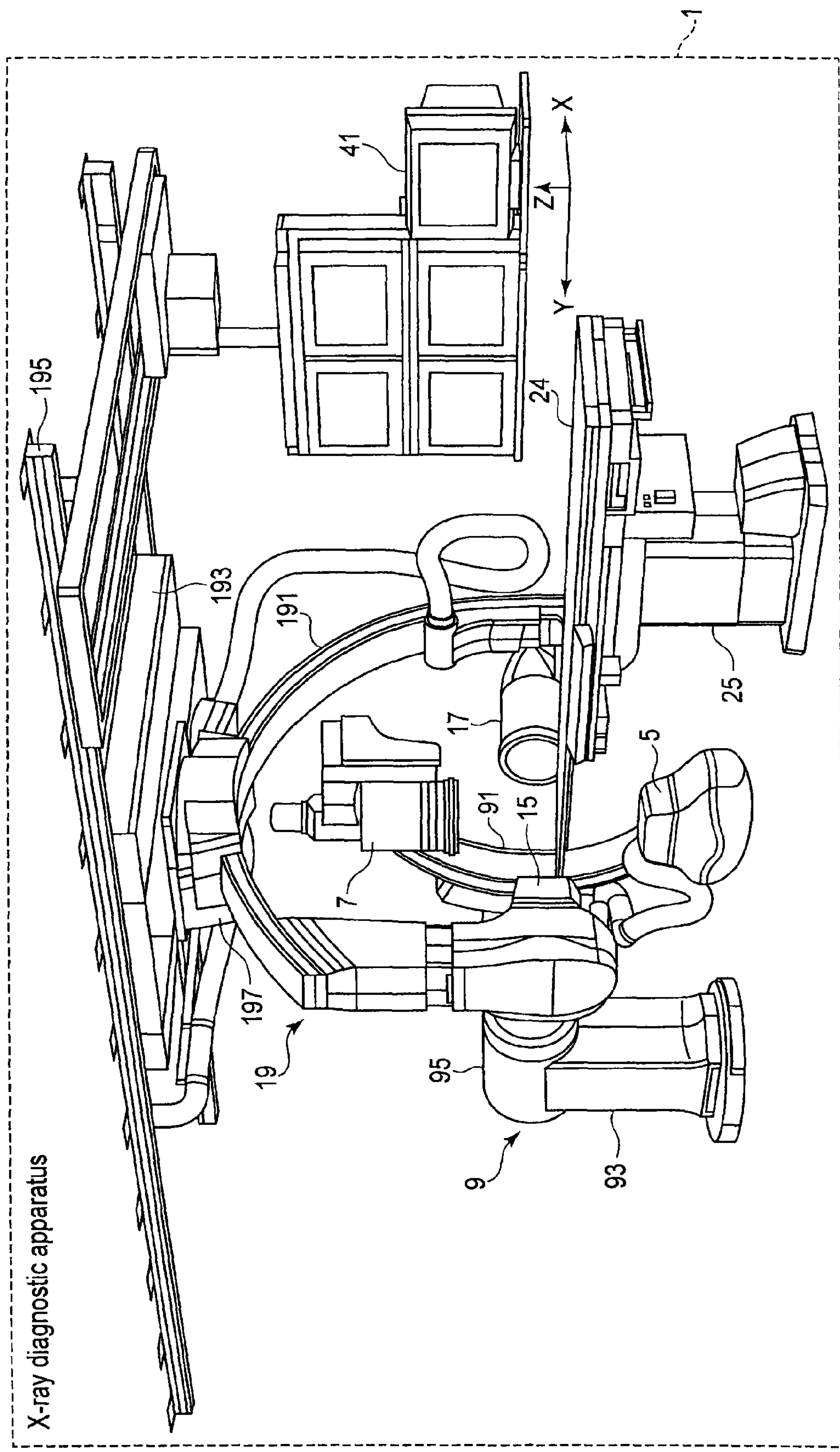
FIG. 1 is a perspective view showing an external appearance of an X-ray diagnostic apparatus according to an embodiment.

In general, according to one embodiment, an X-ray diagnostic apparatus includes a first support mechanism, a second support mechanism, a dose distribution generation unit, a specifying unit, and a display unit.

The first support mechanism supports a first X-ray tube which irradiates an object with first X-rays along a first direction. The second support mechanism supports a second X-ray tube which irradiates the object with second X-rays along a second direction different from the first direction. The dose distribution generation unit generates a first dose distribution concerning the first X-rays and generates a second dose distribution concerning the second X-rays. The specifying unit specifies position states of the first support mechanism and of the second support mechanism and operation states of the first X-ray tube and of the second X-ray tube. The display unit simultaneously displays, with at least two different viewpoints in accordance with the position states and the operation states, a model on which the first dose distribution and the second dose distribution are superimposed.

An X-ray diagnostic apparatus according to an embodiment will be described below with reference to the accompanying drawing. Note that the same reference numerals in the following description denote constituent elements having almost the same functions and arrangements, and a repetitive description will be made when required.

FIG. 1 is a perspective view showing the outer appearance of the X-ray diagnostic apparatus according to this embodiment. As shown in FIG. 1, an X-ray diagnostic apparatus 1 according to the embodiment has a plurality of support mechanisms (biplane structure).

FIG. 2 shows the arrangement of the X-ray diagnostic apparatus 1 according to this embodiment. The X-ray diagnostic apparatus 1 includes a high voltage generation unit 3, a first X-ray tube 5, a first X-ray detector 7, a first support mechanism 9, a first irradiation range limiter 11, a first dosimeter 13, a second X-ray tube 15, a second X-ray detector 17, a second support mechanism 19, second irradiation range limiter 21, a second dosimeter 23, a bed 25 including a top 24, a driving unit 27, an image generation unit 29, an interface unit 31, a storage unit 33, a dose distribution generation unit 35, an input unit 37, a specifying unit 39, a display unit 41, and a control unit 43. FIG. 2 is a block diagram showing the arrangement of the X-ray diagnostic apparatus 1 according to this embodiment.

The high voltage generation unit 3 generates tube currents supplied to the first X-ray tube 5 and the second X-ray tube 15 and tube voltages applied to the first X-ray tube 5 and the second X-ray tube 15. The high voltage generation unit 3 supplies tube currents to the first X-ray tube 5 and the second X-ray tube 15 and applies tube voltages to the first X-ray tube 5 and the second X-ray tube 15 under the control of the control unit 43 (to be described later) in accordance with X-ray imaging conditions (to be described later). The high voltage generation unit 3 outputs, to the specifying unit 39 (to be described later), information indicating whether a tube current is supplied to the first X-ray tube 5 and a tube voltage is applied to it. The high voltage generation unit 3 outputs, to the specifying unit 39 (to be described later), information indicating whether a tube current is supplied to the second X-ray tube 15 and a tube voltage is applied to it.

The first X-ray tube 5 generates X-rays (to be referred to as first X-rays hereinafter) at an X-ray focal point (to be referred to as the first focal point hereinafter) based on the tube current supplied from the high voltage generation unit 3 and the tube voltage applied from the high voltage generation unit 3. The first X-rays generated from the first focal point irradiate an object P through the X-ray radiation window provided on the front surface of the first X-ray tube 5.

The first X-ray detector 7 detects the first X-rays generated from the first X-ray tube 5 and transmitted through the object P. For example, the first X-ray detector 7 has a flat panel detector (to be referred to as the first FPD hereinafter). The first FPD includes a plurality of semiconductor detection elements. Semiconductor detection elements are classified into a direct conversion type and an indirect conversion type. The direct conversion type is a scheme of directly converting incident X-rays into an electrical signal. The indirect conversion type is a scheme of converting incident X-rays into light through a phosphor and converting the light into an electrical signal.

The electrical signal generated by a plurality of semiconductor detection elements upon incidence of the first X-rays is output to an analog to digital converter (to be referred to as an A/D converter hereinafter) (not shown). The A/D converter converts an electrical signal into digital data. The A/D converter outputs the digital data to a preprocessing unit (not shown). Note that an image intensifier may be used as the first X-ray detector 7.

The first support mechanism 9 movably supports the first X-ray tube 5 and the first X-ray detector 7. More specifically, the first support mechanism 9 includes a C-arm 91 and a C-arm support portion 93 in FIG. 1. The first X-ray tube 5 and the first X-ray detector 7 are mounted on the C-arm 91 so as to face each other. The C-arm support portion 93 supports the C-arm 91 so as to make it slidable in a direction (to be referred to as a C direction hereinafter) along the C shape of the C-arm 91.

In addition, the C-arm support portion 93 supports the C-arm 91 so as to make it rotatable almost about a first connecting portion 95 which connects the C-arm 91 to the C-arm support portion 93 in a direction (to be referred to as a C orthogonal direction hereinafter) perpendicular to a C direction. Note that the C-arm support portion 93 can also support the C-arm 91 so as to make it translatable in the short-axis direction (the X direction in FIGS. 1 and 2) and long-axis direction (the Y direction in FIGS. 1 and 2) of the top 24 (to be described later). In addition, the C-arm 91 supports the first X-ray tube 5 and the first X-ray detector 7 so as to make it possible to change the distance (Source Image Distance to be referred to as the first SID hereinafter) between the first focal point and the first X-ray detector 7.

The first irradiation range limiter 11 is provided on the front surface of the X-ray radiation window of the first X-ray tube 5. That is, the first irradiation range limiter 11 is provided between the first X-ray tube 5 and the first X-ray detector 7. The first irradiation range limiter 11 is also called an X-ray movable stop. More specifically, the first irradiation range limiter 11 limits an irradiation range having a maximum aperture (to be referred to as a maximum irradiation range hereinafter) in accordance with an irradiation area on the body surface of the object P which is irradiated with X-rays, in order to prevent any region other than the imaging region desired by an operator from being exposed to the X-rays generated at the first focal point. For example, the first irradiation range limiter 11 limits an irradiation range by moving aperture blades in accordance with an instruction to limit an irradiation range (to be referred to as the first irradiation range hereinafter) which is input via the input unit 37 (to be described later).

More specifically, the first irradiation range limiter 11 includes a plurality of aperture blades movable along one of two axes perpendicular to the first SID and a plurality of aperture blades movable along the other axis. These aperture blades are formed from lead which shields X-rays generated at the first focal point.

Note that the first irradiation range limiter 11 may include a plurality of radiation quality adjustment filters to be inserted into the irradiation range of the first X-rays to reduce the exposure dose to the object P and improve image quality. The plurality of radiation quality adjustment filters respectively have different thicknesses. Note that the radiation quality adjustment filters may be respectively formed from different materials and have the same thickness. The radiation quality adjustment filters reduce low-energy X-ray components (soft radiation components), of the first X-rays, which are easily absorbed by the object P. Alternatively, the radiation quality adjustment filters may reduce high-energy X-ray components, of the first X-rays, which cause a reduction in the contrast of the first medical image generated by the image generation unit 29 (to be described later).

The first dosimeter 13 is provided on the front surface of the first irradiation range limiter 11. That is, the first dosimeter 13 is provided between the first irradiation range limiter 11 and the first X-ray detector 7. The first dosimeter 13 is, for example, an area dosimeter. The first dosimeter 13 measures the integration value of the first X-ray doses (area dose) throughout a predetermined period. The predetermined period is a dose measurement period. A dose measurement period corresponds to a readout period during which the area dose measured by the first dosimeter 13 is read out from the first dosimeter 13. The first dosimeter 13 outputs the area dose (to be referred to as the first X-ray dose hereinafter) read out for each readout period to the storage unit 33 and the dose distribution generation unit 35 (both of which will be described later).

The second X-ray tube 15 generates X-rays (to be referred to as the second X-rays hereinafter) at an X-ray focal point (to be referred to as the second focal point hereinafter) based on the tube current supplied from the high voltage generation unit 3 and the tube voltage applied from the high voltage generation unit 3. The second X-rays generated from the second focal point irradiate the object P through the X-ray radiation window provided on the front surface of the second X-ray tube 15.

The second X-ray detector 17 detects X-rays generated from the second X-ray tube 15 and transmitted through the object P. For example, the second X-ray detector 17 has the second FPD. The electrical signal generated by a plurality of semiconductor detection elements upon incidence of the second X-rays is output to an A/D converter (not shown). The A/D converter converts the electrical signal into digital data. The A/D converter outputs the digital data to a preprocessing unit (not shown). Note that an image intensifier may be used as the second X-ray detector 17.

The second support mechanism 19 movably supports the second X-ray tube 15 and the second X-ray detector 17. More specifically, the second support mechanism 19 includes, for example, an Ω-arm 191 and an Ω-arm support portion 193 in FIG. 1. The second X-ray tube 15 and the second X-ray detector 17 are mounted on the Ω-arm 191 so as to face each other. Note that the Ω-arm support portion 193 supports the Ω-arm 191 so as to make it slidable in a direction (to be referred to as an Ω direction hereinafter) along the Ω-shape of the Ω-arm 191.

In addition, the Ω-arm support portion 193 is installed so as to be movable along rails 195 provided on the ceiling. The rails 195 are provided on the ceiling so as to be parallel to the long-axis direction of the top 24. The Ω-arm support portion 193 supports the Ω-arm 191 so as to make it rotatable almost about a second connecting portion 197 which connects the Ω-arm 191 to the Ω-arm support portion 193 in a direction (to be referred to as an Ω orthogonal direction hereinafter) perpendicular to the Ω direction. Note that the Ω-arm support portion 193 can also support the Ω-arm 191 so as to make it translatable in the short-axis direction (the X direction in FIGS. 1 and 2) and long-axis direction (the Y direction in FIGS. 1 and 2) of the top 24 (to be described later). In addition, the Ω-arm 191 supports the second X-ray tube 15 and the second X-ray detector 17 so as to make it possible to change the distance (Source Image Distance to be referred to as the second SID hereinafter) between the second focal point and the second X-ray detector 17.

The second irradiation range limiter 21 is provided on the front surface of the X-ray radiation window of the second X-ray tube 15. That is, the second irradiation range limiter 21 is provided between the second X-ray tube 15 and the second X-ray detector 17. The second irradiation range limiter 21 is also called an X-ray movable stop. More specifically, the second irradiation range limiter 21 limits a maximum irradiation range in accordance with an irradiation area on the body surface of the object P which is irradiated with X-rays, in order to prevent any region other than the imaging region desired by the operator from being exposed to the X-rays generated at the second focal point. For example, in accordance with an instruction to limit an irradiation range (to be referred to as the second irradiation range hereinafter) which is input via the input unit 37 (to be described later), the second irradiation range limiter 21 limits the irradiation range by moving aperture blades.

More specifically, the second irradiation range limiter 21 includes a plurality of aperture blades movable along one of two axes perpendicular to the second SID and a plurality of aperture blades movable along the other axis. These aperture blades are formed from lead which shields X-rays generated from at the second focal point. Note that the second irradiation range limiter 21 may include a plurality of radiation quality adjustment filters to be inserted into the irradiation range of the second X-rays to reduce the exposure dose to the object P and improve image quality.

The second dosimeter 23 is provided on the front surface of the second irradiation range limiter 21. That is, the second dosimeter 23 is provided between the second irradiation range limiter 21 and the second X-ray detector 17. The second dosimeter 23 is, for example, an area dosimeter. The second dosimeter 23 measures the integration value of X-ray doses (area dose) throughout a predetermined period. The second dosimeter 23 outputs the area dose (to be referred to as the second X-ray dose hereinafter) read out for each readout period to the storage unit 33 and the dose distribution generation unit 35 (both of which will be described later).

Note that the first dosimeter 13 and the second dosimeter 23 may not be mounted on the X-ray diagnostic apparatus 1. In this case, the X-ray dose measured on the top 24 in advance is stored in the storage unit 33.

The bed 25 includes the top 24 on which the object P is placed. The object P is placed on the top 24.

The driving unit 43 drives the first support mechanism 9, the second support mechanism 19, and the bed 25 under the control of the control unit 43. More specifically, the driving unit 27 supplies a driving signal corresponding to a control signal from the control unit 43 to the C-arm support portion 93 to slide the C-arm 91 in the C direction and rotate it in the C orthogonal direction. The driving unit 27 supplies a driving signal corresponding to a control signal from the control unit 43 to the Ω-arm support portion 193 to slide the Ω-arm 191 in the Ω direction and rotate it in the Ω orthogonal direction.

At the time of X-ray imaging, the object P placed on the top 24 is arranged between the first X-ray tube 5 and the first X-ray detector 7 and between the second X-ray tube 15 and the second X-ray detector 17. The driving unit 27 outputs the position of the first X-ray tube 5 (or the position of the first support mechanism 9) relative to the top 24 and the position of the second X-ray tube 15 (or the position of the second support mechanism 19) relative to the top 24 to the specifying unit 39 (to be described later) and the like.

The driving unit 27 moves the top 24 by driving the top 24 under the control of the control unit 43 (to be described later). More specifically, the driving unit 27 slides the top 24 in the short-axis direction (the X direction in FIGS. 1 and 2) of the top 24 or the long-axis direction (the Y direction in FIGS. 1 and 2) of the top 24 based on a control signal from the control unit 43. The driving unit 27 also moves the top 24 upward and downward in the vertical direction (the Z direction in FIGS. 1 and 2). In addition, the driving unit 27 may rotate the top 24 to tilt it about at least one of the long-axis direction and the short-axis direction as a rotation axis (the X-axis or the Y-axis in FIG. 1). The driving unit 27 outputs the position of the top 24 to the specifying unit 39 (to be described later).

The driving unit 27 outputs the position (to be referred to as the first position hereinafter) of the first support mechanism 9 and the position (to be referred to as the second position hereinafter) of the second support mechanism 19 to the specifying unit 39 (to be described later). Note that the first position may be output from the first support mechanism 9 to the specifying unit 39. In addition, the second position may be output from the second support mechanism 19 to the specifying unit 39.

The driving unit 27 outputs the relative positional relationship (to be referred to as the first relative position hereinafter) between the first X-ray tube 5 and the top 24 to the dose distribution generation unit 35 (to be described later). The driving unit 27 outputs the relative positional relationship (to be referred to as the second relative position hereinafter) between the second X-ray tube 15 and the top 24 to the dose distribution generation unit 35 (to be described later).

The first relative position is, for example, the angle (tilt) of the C-arm 91 relative to the top 24 or the sliding angle of the C-arm 91 (to be referred to as the arm angle). The tilt or the arm angle is the Euler angle with reference to the isocenter relative to the object P. Note that the driving unit 27 may drive the first X-ray detector 7 to arbitrarily rotate it in accordance with the position of the first support mechanism 9, the angle of the C-arm 91, or the like.

The second relative position is, for example, the angle (tilt) of the Ω-arm 191 relative to the top 24 or the sliding arm angle of the Ω-arm 191. The tilt or the arm angle is the Euler angle with reference to the isocenter relative to the object P. Note that the driving unit 27 may drive the second X-ray detector 17 to arbitrarily rotate it in accordance with the position of the second support mechanism 19, the angle of the Ω-arm 191, or the like.

The preprocessing unit (not shown) executes preprocessing for the digital data output from the first X-ray detector 7 and the second X-ray detector 17. Preprocessing includes correction of sensitivity unevenness between the channels in the first X-ray detector 7 and the second X-ray detector 17 and correction concerning an excessive decrease in signal level or data omission due to an X-ray absorber such as a metal. The preprocessed digital data is output to the image generation unit 29 (to be described later).

The image generation unit 29 generates two X-ray images corresponding to the first and second relative positions based on the preprocessed digital data. The image generation unit 29 outputs the generated X-ray images to the storage unit 33 and the display unit 41 (both of which will be described later).

The interface unit 31 is, for example, an interface for a network and an external storage device (not shown). Data such as X-ray images obtained by the X-ray diagnostic apparatus 1, analysis results, and the like can be transferred to another apparatus via the interface unit 31 and the network.

The storage unit 33 stores various types of X-ray images generated by the image generation unit 29, control programs for the X-ray diagnostic apparatus 1, a diagnosis protocol, the operator's instructions sent from the input unit 37 (to be described later), various types of data groups such as imaging conditions and fluoroscopy conditions concerning X-ray imaging, various types of data sent via the interface unit 31 and a network, the first X-ray dose, the second X-ray dose, and the like. The storage unit 33 may also store the first relative position, the second relative position, the first irradiation range, and the second irradiation range.

The storage unit 33 stores X-ray irradiation conditions (to be referred to as the first X-ray conditions hereinafter) concerning the generation of the first X-rays. The storage unit 33 stores X-ray irradiation conditions (to be referred to as the second X-ray conditions hereinafter) concerning the generation of the second X-rays. The first X-ray irradiation conditions include conditions associated with the radiation quality of the first X-rays (a tube voltage, tube current, and the like), an irradiation time, an irradiation interval, the aperture (the first irradiation range) of the first irradiation range limiter 11, the product (to be referred to as a tube current time product (mAs) hereinafter) of a tube current (mA) and an irradiation time (s), the thickness of the radiation quality adjustment filter (or the type of radiation quality adjustment filter) selected via the input unit 37, an imaging field of view (Field of view: FOV), and an irradiation rate (X-ray irradiation count per sec).

The second X-ray conditions include conditions associated with the radiation quality of the second X-rays (a tube voltage, tube current, and the like), an irradiation time, an irradiation interval, the aperture (second irradiation range) of the second irradiation range limiter 21, a tube current time product (mAs), the thickness of the radiation quality adjustment filter (or the type of radiation quality adjustment filter) selected via the input unit 37, an imaging field of view (Field of view: FOV), and an irradiation rate. Note that of the first and second X-ray conditions, the thickness (type) of the radiation quality adjustment filter, an irradiation time, and the like may be set via the input unit 37 (to be described later), as needed.

The storage unit 33 stores geometrical conditions (to be referred to as the first geometrical conditions hereinafter) for each time of irradiation (generation) of the first X-rays. The first geometrical conditions include the first reference position, the position of the top 24, the position of the C-arm 91, the angle of the C-arm 91, the irradiation direction (to be referred to as the first direction hereinafter) of the first X-rays, the first SID, and the first FPD rotational angle. The first reference position is, for example, a position 15 cm away from the isocenter of the X-ray diagnostic apparatus 1 toward the first focal point. Note that the storage unit 33 may store the reference position and a correspondence table between the apertures of the first irradiation range limiter 11 and irradiation areas (to be referred to as the first irradiation areas hereinafter) at the reference position. The storage unit 33 may also store an irradiation area for each time of irradiation of the first X-rays.

The storage unit 33 stores geometrical conditions (to be referred to as the second geometrical conditions hereinafter) for each time of irradiation (generation) of the second X-rays. The second geometrical conditions include the second reference position, the position of the top 24, the position of the Ω-arm 191, the angle of the Ω-arm 191, the irradiation direction (to be referred to as the second direction hereinafter) of the second X-rays, the second SID, and the second FPD rotational angle. The second reference position is, for example, a position 15 cm away from the isocenter of the X-ray diagnostic apparatus 1 toward the second focal point. Note that the storage unit 33 may store the reference position and a correspondence table between the apertures of the second irradiation range limiter 21 and irradiation areas (to be referred to as the second irradiation areas hereinafter) at the reference position. The storage unit 33 may also store an irradiation area for each time of irradiation of the second X-rays.

The storage unit 33 stores a patient model to be used by the dose distribution generation unit 35 (to be described later). Note that the storage unit 33 may also store a dose distribution generation program for generating a dose distribution at a predetermined reference position. The storage unit 33 also stores the dose distribution generated by the dose distribution generation unit 35 (to be described later). Note that the storage unit 33 may store the X-ray doses measured in advance on the top 24.

The dose distribution generation unit 35 generates a dose distribution (to be referred to as the first dose distribution hereinafter) at the first reference position based on the first X-ray dose, the first geometrical conditions, the first X-ray conditions, and the first irradiation area. The first dose distribution is the distribution of incident skin doses of the first X-rays with which the body surface of the object P is irradiated. The dose distribution generation unit 35 outputs the generated first dose distribution to the display unit 41 (to be described later), together with the first geometrical conditions.

More specifically, the dose distribution generation unit 35 calculates an air kerma (to be referred to as the first air kerma hereinafter) at the first reference position based on the first geometrical conditions, the first X-ray dose, and the first irradiation area. The dose distribution generation unit 35 reads out the patient model from the storage unit 33. The dose distribution generation unit 35 calculates a dose (to be referred to as the first incident skin dose hereinafter) at an irradiation position on the patient model based on the calculated first air kerma, the first irradiation area, the first geometrical conditions.

Note that when calculating the first incident skin dose from the first air kerma, the dose distribution generation unit 35 can also calculate the first incident skin dose in consideration of the influence of backscattered radiation. The dose distribution generation unit 35 generates the first dose distribution by mapping the first incident skin dose at the irradiation position on the patient model.

The dose distribution generation unit 35 generates a dose distribution (to be referred to as the second dose distribution hereinafter) at the second reference position based on the second X-ray dose, the second geometrical conditions, the second X-ray conditions, and the second irradiation area. The second dose distribution is the distribution of incident skin doses of the second X-rays with which the body surface of the object P is irradiated. The dose distribution generation unit 35 outputs the generated second dose distribution to the display unit 41 (to be described later), together with the second geometrical conditions.

More specifically, the dose distribution generation unit 35 calculates an air kerma (to be referred to as the second air kerma hereinafter) at the second reference position based on the second geometrical conditions, the second X-ray dose, and the second irradiation area. The dose distribution generation unit 35 calculates a dose (to be referred to as the second incident skin dose hereinafter) at an irradiation position on the patient model based on the calculated second air kerma, the second irradiation area, the second geometrical conditions.

Note that when calculating the second incident skin dose from the second air kerma, the dose distribution generation unit 35 can also calculate the second incident skin dose in consideration of the influence of backscattered radiation. The dose distribution generation unit 35 generates the second dose distribution by mapping the second incident skin dose at the irradiation position on the patient model.

Note that if the first dosimeter 13 and the second dosimeter 23 are not mounted in the X-ray diagnostic apparatus 1, the dose distribution generation unit 35 reads out X-ray doses measured in advance from the storage unit 33. The dose distribution generation unit 35 generates the first dose distribution based on the readout X-ray doses, the first X-ray conditions, the first geometrical conditions, and the first irradiation area. The dose distribution generation unit 35 generates the second dose distribution based on the readout X-ray doses, the second X-ray conditions, the second geometrical conditions, and the second irradiation area.

More specifically, the dose distribution generation unit 35 converts the X-ray dose read out by using the first X-ray conditions into an X-ray dose corresponding to the first X-ray conditions. The dose distribution generation unit 35 then corrects the converted X-ray dose in accordance with the thickness (to be referred to as the first thickness hereinafter) of the top 24 along the first X-rays. The first thickness is decided by the dose distribution generation unit 35 based on, for example, the first relative position in the first geometrical conditions. The dose distribution generation unit 35 generates the first dose distribution based on the corrected X-ray dose and the first irradiation area.

In addition, the dose distribution generation unit 35 converts the X-ray dose read out by using the second X-ray conditions into an X-ray dose corresponding to the second X-ray conditions. The dose distribution generation unit 35 then corrects the converted X-ray dose in accordance with the thickness (to be referred to as the second thickness hereinafter) of the top 24 along the second X-rays. The second thickness is decided by the dose distribution generation unit 35 based on, for example, the second relative position in the second geometrical conditions. The dose distribution generation unit 35 generates the second dose distribution based on the corrected X-ray dose and the second irradiation area.

The input unit 37 inputs X-ray irradiation conditions such as the first and second X-ray conditions, the imaging position based on each of the first and second X-ray tubes, the first and second irradiation ranges, the first and second directions, and the like. More specifically, the input unit 37 inputs various types of instructions, commands, information, selections, and settings from the operator to the X-ray diagnostic apparatus 1. An imaging position is defined by, for example, an angle relative to the isocenter. For example, if the starting point in the first oblique direction (RAO), second oblique direction (LAO), cranial direction (CRA), and caudal direction (CAU) is the imaging position and the origin of the three orthogonal axes in FIG. 2 is the isocenter, the fluoroscopy position angle at the starting point is 0°. Note that the first direction may be specified by the specifying unit 39 based on the first relative position in the first geometrical conditions. In addition, the second direction may be specified by the specifying unit 39 based on the second relative position in the second geometrical conditions.

The input unit 37 includes a trackball, mouse, and keyboard for, for example, setting a region of interest. The input unit 37 includes a switch button for switching the first and second displays (to be described later). The input unit 37 detects the coordinates of the cursor displayed on a display screen and outputs the detected coordinates to the control unit 43 (to be described later). Note that the input unit 37 may be a touch panel provided to cover the display screen. In this case, the input unit 37 detects a touched and designated coordinates by a coordinate reading principle such as an electromagnetic induction scheme, magnetostriction scheme, or a pressure-sensitive scheme, and outputs the detected coordinates to the control unit 43.

The specifying unit 39 specifies the position state of the first support mechanism 9 based on the first position. More specifically, the specifying unit 39 specifies, based on the first position, whether the first support mechanism 9 is located at a retracting position. A retracting position is also called a park position. A park position is a position where the first support mechanism 9 and the second support mechanism 19 retract to a place which is safe (non-interfering) with respect to the operator and the object P and is irrelevant to X-ray imaging. When the first support mechanism 9 is arranged at the park position, the specifying unit 39 outputs display switching information to the display unit 41 (to be described later).

The specifying unit 39 specifies the position state of the second support mechanism 19 based on the second position. More specifically, the specifying unit 39 specifies, based on the second position, whether the second support mechanism 19 is located at the park position. When the second support mechanism 19 is arranged at the park position, the specifying unit 39 outputs display switching information to the display unit 41 (to be described later).

The specifying unit 39 specifies the operation state of the first X-ray tube 5 based on an output from the high voltage generation unit 3. More specifically, the specifying unit 39 specifies, based on an output from the high voltage generation unit 3, whether the first X-ray tube 5 is operating. If the first X-ray tube 5 is not operating, the specifying unit 39 outputs display switching information to the display unit 41 (to be described later).

The specifying unit 39 specifies the operation state of the second X-ray tube 15 based on an output from the high voltage generation unit 3. More specifically, the specifying unit 39 specifies, based on an output from the high voltage generation unit 3, whether the second X-ray tube 15 is operating. If the second X-ray tube 15 is not operating, the specifying unit 39 outputs display switching information to the display unit 41 (to be described later).

The display unit 41 displays the X-ray image generated by the image generation unit 29. The display unit 41 displays an input screen concerning inputs such as an imaging position, the first X-ray conditions, the second X-ray conditions, and the like.

The display unit 41 displays the first and second dose distributions generated by the dose distribution generation unit 35, together with the patient model, in different display areas (this operation will be referred to as the first display hereinafter), respectively. More specifically, the display unit 41 displays the superimposed image obtained by superimposing the first irradiation field of the first X-rays, the first dose distribution, the second irradiation field of the first X-rays, and the second dose distribution on the patient model. In the first display, the first dose distribution is displayed, with the first focal point being a viewpoint and the first direction being a line-of-sight direction. In the first display, the second dose distribution is displayed, with the second focal point being a viewpoint and the second direction being a line-of-sight direction.

The display unit 41 displays at least one of the first and second dose distributions, together with the patient model, in one display area (this operation will be referred to as the second display hereinafter). More specifically, in the second display, at least one of the first and second dose distributions is displayed, with a predetermined position a predetermined distance below the back surface of the top 24 (the surface facing the placement surface on which the object P is placed) being a viewpoint and a predetermined direction from a predetermined position to the body surface of the object P being a line-of-sight direction. Note that it is possible to arbitrarily set a viewpoint position and a line-of-sight direction in the second display via the input unit 37.

The display unit 41 alternately switches and displays the first and second displays in accordance with display switching information. More specifically, the display unit 41 displays the first and second dose distributions in the first display when the first support mechanism 9 and the second support mechanism 19 execute X-ray imaging. The display unit 41 switches and displays the first and second displays in accordance with the position states of the first and second support mechanisms 9 and 19 and the operation states of the first and second X-ray tubes 5 and 15.

When, for example, the first support mechanism 9 is arranged at the park position or the first X-ray tube 5 is not operating, the display unit 41 displays the superimposed image obtained by superimposing the second dose distribution on the patient model as the second display. In addition, when the second support mechanism 19 is arranged at the park position or the second X-ray tube 15 is not operating, the display unit 41 displays the superimposed image obtained by superimposing the first dose distribution on the patient model as the second display. Note that when no display switching information has been output, the display unit 41 maintains the first display.

Note that the display unit 41 may use a cylinder covering the patient model instead of the patient model. In this case, the display unit 41 displays, on the surface of the cylinder, the first irradiation field, the first dose distribution, the second irradiation field, and the second dose distribution. In addition, the display unit 41 may use a predetermined shape corresponding to an imaging region instead of the patient model. The predetermined shape is, for example, spherical when an imaging region is a head region, and cylindrical when an imaging region is an abdominal region. In this case, the display unit 41 displays, on the surface of the predetermined shape, the first irradiation field, the first dose distribution, the second irradiation field, and the second dose distribution.

Figure 3:
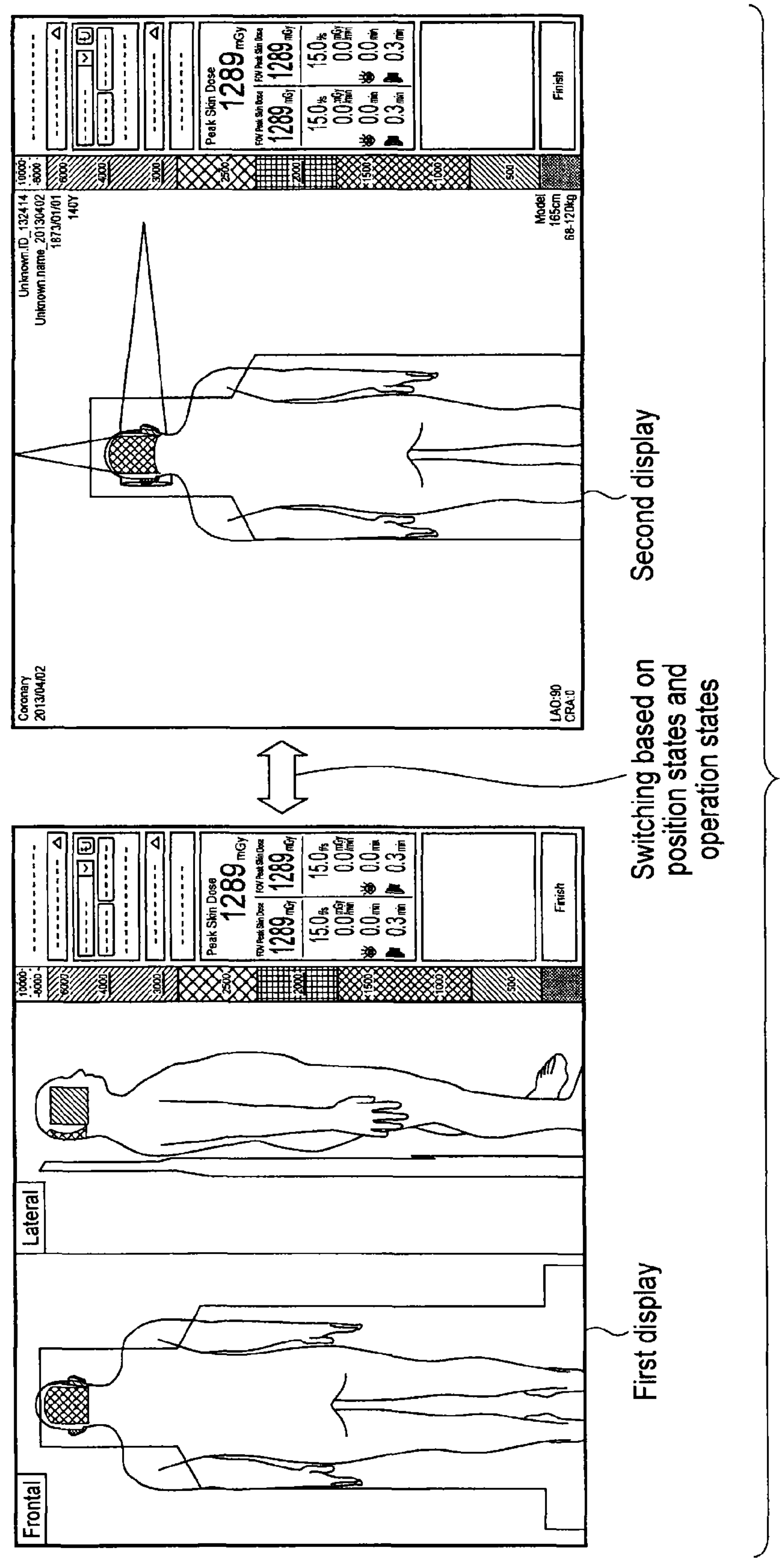
FIG. 3 shows the first and second displays switched and displayed on a display unit according to this embodiment.

FIG. 3 shows an example of the first and second displays alternately switched and displayed on the display unit 41. As shown in FIG. 3, when X-ray imaging is executed with respect to the object P from two different directions, the display unit 41 displays the first and second dose distributions as the first display. Subsequently, the display unit 41 switches the first and second displays in accordance with the position states of the first support mechanism 9 and the second support mechanism 19 and the operation states of the first X-ray tube 5 and the second X-ray tube 15. Note that it is possible to properly switch the first and second displays in accordance with the operation of a switch button of the input unit 37.

The control unit 43 includes a CPU (Central Processing Unit) and a memory (neither of which is shown). The control unit 43 temporarily stores, in a memory (not shown), information such as the operator's instruction sent from the input unit 37, the imaging position, the imaging direction (first direction) of the first X-ray tube 5, the imaging direction (second direction) of the second X-ray tube 15, the first irradiation range, the second irradiation range, the first X-ray conditions, and the second X-ray conditions. The control unit 43 controls the high voltage generation unit 3, the first X-ray detector 7, the second X-ray detector 17, the first irradiation range limiter 11, the second irradiation range limiter 21, the driving unit 27, and the like to execute X-ray imaging in accordance with the operator's instruction, the imaging position, the first direction, the second direction, the first irradiation range, the second irradiation range, the first X-ray conditions, the second X-ray conditions, and the like stored in the memory. The control unit 43 reads out the dose distribution generation program stored in the storage unit 33 and expands the program in the memory. The control unit 43 controls the dose distribution generation unit 35, the display unit 41, and the like in accordance with the dose distribution generation program expanded in the memory.

(Dose Distribution Switching Function)

The dose distribution switching function is a function of alternately switching the first and second displays in accordance with the position states of the first support mechanism 9 and the second support mechanism 19 and the operation states of the first X-ray tube 5 and the second X-ray tube 15. Processing associated with the dose distribution switching function (to be referred to as dose distribution switching processing hereinafter) will be described below.

FIG. 4 is a flowchart showing an example of a procedure for dose distribution switching processing.

X-ray imaging is executed with respect to the object P (step Sa1). The first and second X-ray doses are measured (step Sa2). The first dose distribution is generated based on the first X-ray dose, the first X-ray conditions, the first irradiation area, and the first geometrical conditions (step Sa3). The second dose distribution is generated based on the second X-ray dose, the second X-ray conditions, the second irradiation area, and the second geometrical conditions (step Sa4). The first and second dose distributions are displayed as the first display in different display areas, together with the patient model (step Sa5). The position states of the first support mechanism 9 and the second support mechanism 19 and the operation states of the first X-ray tube 5 and the second X-ray tube 15 are specified (step Sa6).

If the first support mechanism 9 or the second support mechanism 19 is arranged at the park position (step Sa7), a dose distribution concerning the support mechanism at a non-park position is displayed as the second display, together with the patient model (step Sa8). After step Sa8, the processing in steps Sa1 to Sa7 is executed again.

If the first support mechanism 9 or the second support mechanism 19 is not arranged at the park position (step Sa7), it is specified whether the first X-ray tube 5 or the second X-ray tube 15 is operating (step Sa9). If the first X-ray tube 5 or the second X-ray tube 15 is not operating (step Sa9), the processing in steps Sa1 to Sa8 is executed again.

If the first X-ray tube 5 and the second X-ray tube 15 are simultaneously irradiating the object P with X-rays (step Sa9), the processing in steps Sa2 to Sa7 is repeated. That is, if the first X-ray tube 5 and the second X-ray tube 15 are simultaneously irradiating the object with X-rays, the first and second dose distributions are displayed as the first display on the display unit 41. If the first X-ray tube 5 and the second X-ray tube 15 are not simultaneously irradiating the object with X-rays (step Sa9), it is determined whether one of the first X-ray tube 5 and the second X-ray tube 15 is irradiating the object with X-rays (step Sa10).

If one of the first X-ray tube 5 and the second X-ray tube 15 is irradiating the object with X-rays (step Sa10), a dose distribution concerning the X-rays generated by the X-ray tube which is irradiating the object with X-rays is displayed as the second display on one screen, together with the patient model (step Sa11). If neither of the first X-ray tube 5 nor the second X-ray tube 15 is irradiating the object with X-rays (step Sa10), it is determined whether X-ray imaging is complete (step Sa12). If X-ray imaging is not complete after the processing in step Sa10 or Sa11 (step Sa12), the processing in steps Sa1 to Sa11 is repeated.

(First Modification)

A difference from the embodiment is that as the second display, a dose distribution concerning the X-ray tube which is generating X-rays or a dose distribution with a large irradiation dose per unit time is displayed.

The specifying unit 39 specifies the operation states of the first X-ray tube 5 and the second X-ray tube 15 in the second display. More specifically, when the second display is executed, the specifying unit 39 specifies, as the operation state of the first X-ray tube 5, whether the first X-ray tube 5 is generating X-rays. When the second display is executed, the specifying unit 39 specifies, as the operation state of the second X-ray tube 15, whether the second X-ray tube 15 is generating X-rays. That is, the specifying unit 39 specifies one of the first X-ray tube 5 and the second X-ray tube 15 which is operating. The specifying unit 39 then specifies a dose distribution corresponding to one of the first X-ray tube 5 and the second X-ray tube 15 which is operating.

The specifying unit 39 specifies, based on the first and second dose distributions, a dose distribution with a larger irradiation dose per unit time. More specifically, the specifying unit 39 decides an irradiation dose (to be referred to as the first irradiation dose hereinafter) per unit time based on the first dose distribution. The specifying unit 39 decides an irradiation dose (to be referred to as the second irradiation dose hereinafter) per unit time based on the second dose distribution. The specifying unit 39 compares the first irradiation dose with the second irradiation dose. The specifying unit 39 specifies one of the first and second irradiation doses which corresponds to a larger irradiation dose. The specifying unit 39 outputs the information of the specified dose distribution (to be referred to as specified information hereinafter) to the display unit 41.

Note that the first and second irradiation doses each are not limited to an irradiation dose per unit time. For example, the specifying unit 39 may specify an irradiation dose in a predetermined time interval (e.g., a readout period of the first dosimeter 13) as the first irradiation dose based on the first X-ray dose. The the specifying unit 39 may also specify an irradiation dose in a predetermined time interval (e.g., a readout period of the second dosimeter 23) as the second irradiation dose based on the second X-ray dose.

Upon receiving specified information from the specifying unit 39 in the second display, the display unit 41 displays the specified dose distribution as the second display. Note that if both the first X-ray tube 5 and the second X-ray tube 15 are operating, the display unit 41 displays, as the second display, a dose distribution corresponding to a larger one of the first and second irradiation doses.

Figure 5:
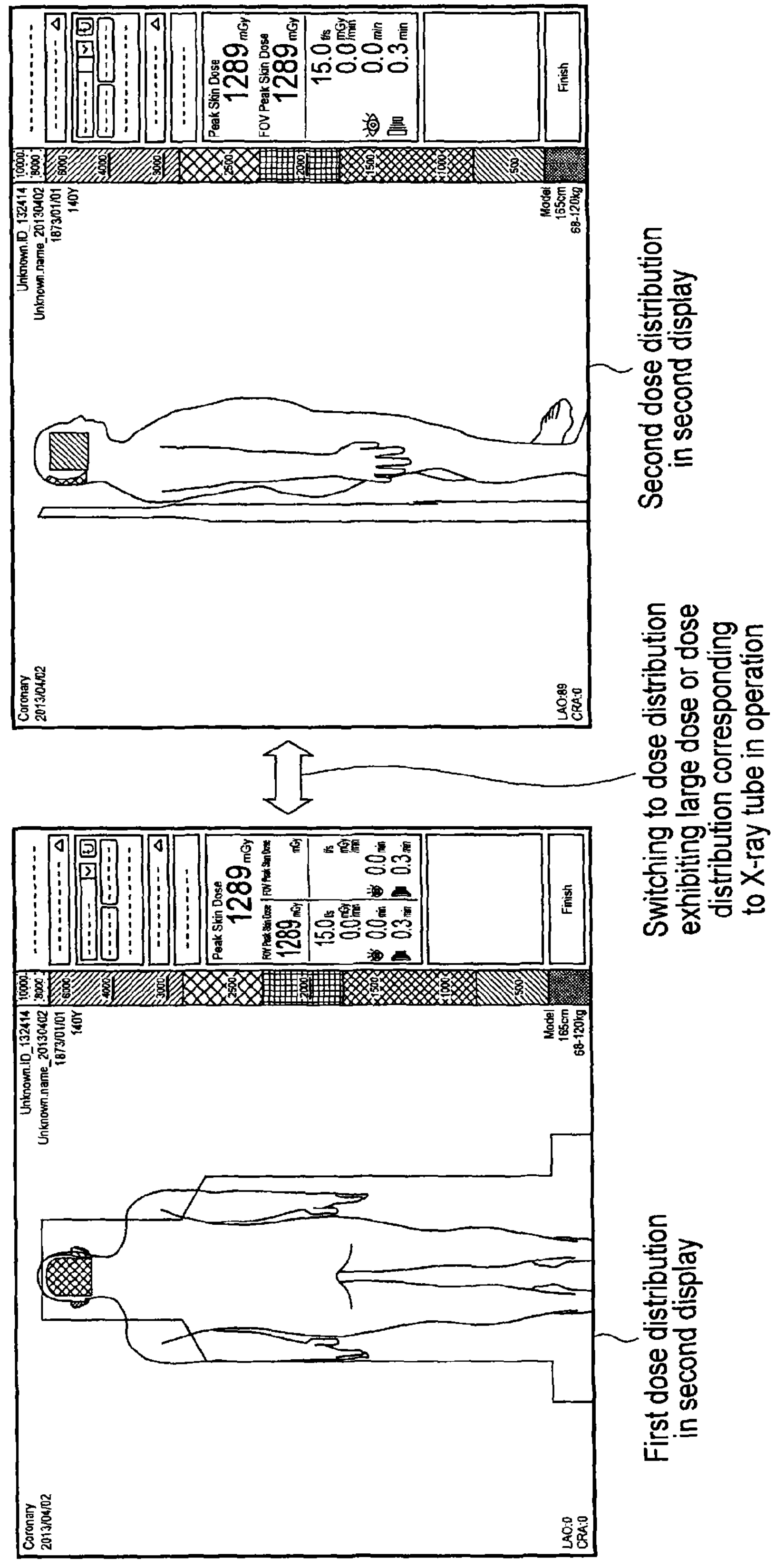
FIG. 5 shows an example of switching between dose distributions to be displayed as the second display based on specified information according to the first modification of this embodiment.

FIG. 5 shows an example of switching between dose distributions to be displayed as the second display based on specified information. The left view in FIG. 5 shows the second display before specified information is input to the display unit 41, and corresponds to an example (the right view in FIG. 3) of the second display displayed in the processing in step Sa8 or Sa10 in FIG. 4. The right view in FIG. 5 shows an example of a switched dose distribution in the second display after specified information is input to the display unit 41.

(Dose Distribution Switching Function)

The dose distribution switching function according to this modification is a function of displaying a specified dose distribution as the second display when specified information is input from the specifying unit 39.

Figure 6:
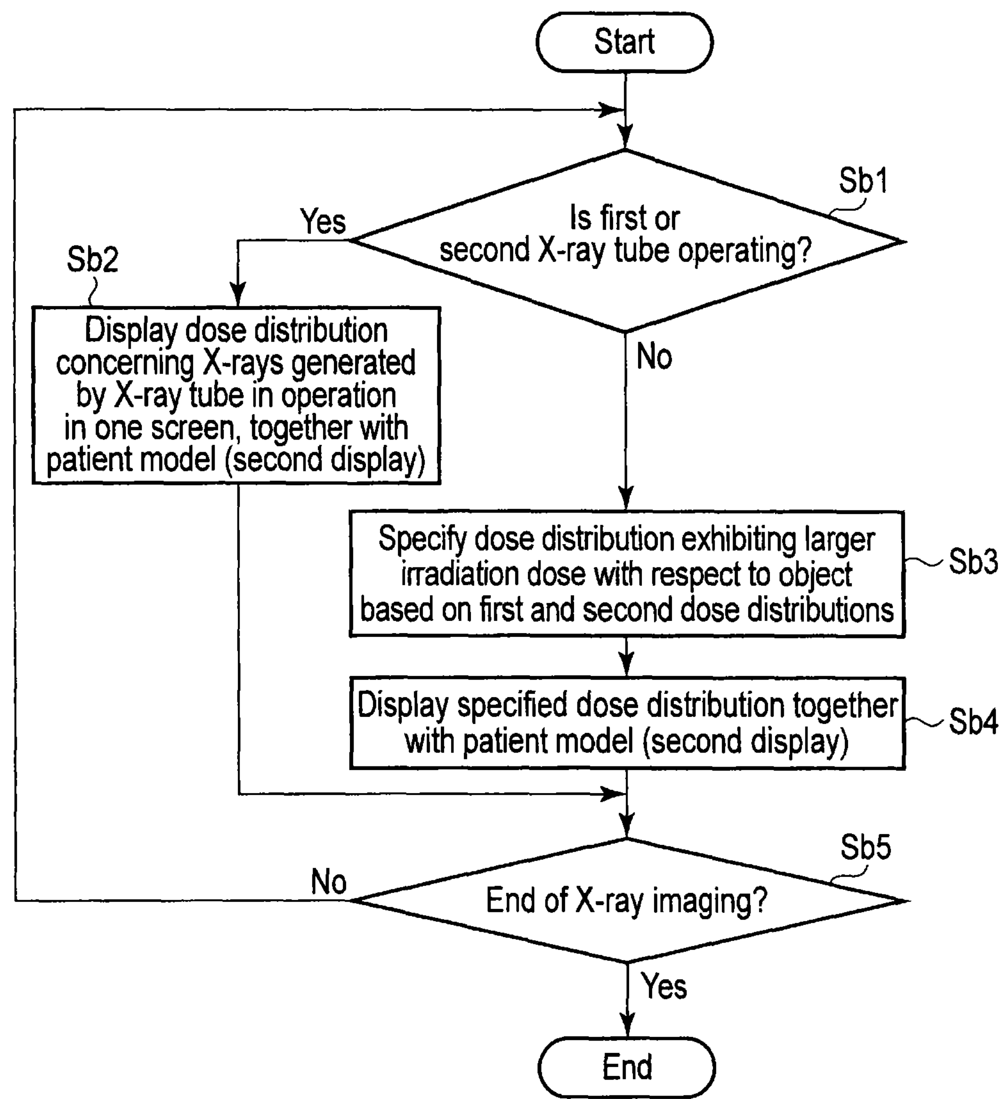
FIG. 6 is a flowchart showing an example of a procedure for dose distribution switching processing associated with a dose distribution switching function according to the first modification of this embodiment.

FIG. 6 is a flowchart showing an example of a procedure for dose distribution switching processing according to the dose distribution switching function. Note that the flowchart of FIG. 6 may be executed following step Sa10 in the flowchart of FIG. 4.

If the first X-ray tube 5 or the second X-ray tube 15 is operating (step Sb1), a dose distribution concerning the X-rays generated by the X-ray tube in operation is displayed as the second display on one screen, together with the patient model (step Sb2). If neither the first X-ray tube 5 nor the second X-ray tube 15 is operating (step Sb1), a dose distribution concerning a larger irradiation dose of the object P based on the first and second dose distributions is specified (step Sb3).

More specifically, the first irradiation dose is generated based on the first dose distribution. The second irradiation dose is generated based on the second dose distribution. The first and second irradiation doses are compared with each other. A dose distribution concerning a larger one of the first and second irradiation doses is specified. The specified dose distribution is displayed as the second display, together with the patient model (step Sb3). The processing in steps Sb1 to Sb3 is repeated until X-ray imaging of the object P is complete (step Sb4).

(Second Modification)

A difference from the embodiment and the first modification is that the first and second dose distributions are repeatedly displayed in the second display in ascending order of irradiation doses of the object P at predetermined time intervals.

The storage unit 33 stores a predetermined time interval. The predetermined time interval corresponds to a display interval at which the first and second dose distributions are switched and displayed. More specifically, the predetermined time interval is, for example, several sec to several ten sec. The storage unit 33 may also store a repeated display count (to be referred to as a predetermined count hereinafter) when the first and second dose distributions are repeatedly switched and displayed.

The specifying unit 39 specifies, based on the first and second dose distributions, the ascending order of integrated irradiation doses of the object P with respect to the first and second dose distributions. In this case, an integrated irradiation dose is the one obtained in an X-ray irradiation period with respect to the object P. More specifically, the specifying unit 39 specifies an integrated irradiation dose (to be referred to as the first integrated irradiation dose hereinafter) based on the first X-ray irradiation period of the first X-ray tube 5 and the first dose distribution. The specifying unit 39 specifies an integrated irradiation dose (to be referred to as the second integrated irradiation dose hereinafter) based on the second X-ray irradiation period of the second X-ray tube 15 and the second dose distribution.

The specifying unit 39 specifies, based on the first and second integrated irradiation doses, the ascending order of integrated irradiation doses of the object P with respect to the first and second dose distributions. The specifying unit 39 outputs the specified order to the display unit 41.

Upon receiving the specified order from the specifying unit 39, the display unit 41 repeatedly displays the first and second dose distributions as the second display at predetermined time intervals in accordance with the specified order.

FIG. 7 shows an example of switching between dose distributions to be displayed as the second display based on the specified order. The left view in FIG. 7 shows the second display before the specified order is input to the display unit 41 and corresponds to an example of the second display (the right view in FIG. 3) displayed in the processing in step Sa8 or Sa10 in FIG. 4. The left view in FIG. 7 shows a dose distribution when the object P is seen from below the top 24 (predetermined viewpoint) along a predetermined line-of-sight direction. The right view in FIG. 7 shows an example of a switched dose distribution (one of the first and second dose distributions which exhibits a smaller integrated irradiation dose) after the order specified in the second display is input to the display unit 41. The lower right view in FIG. 7 shows an example of a switched dose distribution (one of the first and second dose distributions which exhibits a larger integrated irradiation dose) after the lapse of a predetermined time interval since the display of the right view in FIG. 7.

(Dose Distribution Switching Function)

The dose distribution switching function according to this modification is a function of displaying dose distributions in ascending order of integrated irradiation doses as the second display when a specified order is input from the specifying unit 39.

FIG. 8 is a flowchart showing an example of a procedure for dose distribution switching processing according to the dose distribution switching function. Note that the flowchart of FIG. 8 may be executed following, for example, step Sa10 in the flowchart of FIG. 4.

The first integrated irradiation dose is specified based on the first dose distribution (step Sc1). The second integrated irradiation dose is specified based on the second dose distribution (step Sc2). The ascending order of integrated irradiation doses is specified with respect to the first and second dose distributions based on the first and second integrated irradiation doses (step Sc3). The first and second dose distributions are displayed in accordance with the specified order as the second display at predetermined time intervals (step Sc4). Note that after step Sc4, the first and second dose distributions may be switched and displayed over a predetermined count. If X-ray imaging is not complete (step Sc5), X-ray imaging is executed again with respect to the object P (step Sc6). The processing in steps Sc1 to Sc5 is then executed.

(Third Modification)

A difference from the embodiment and the first and second modifications is that the display area of the display unit 41 is divided into at least three display areas, and at least one of the first and second dose distributions is displayed in each of the three display areas.

The storage unit 33 stores the three-division display mode of dividing the display area of the display unit 41 into three display areas. The storage unit 33 stores the display layout of the divided three display areas in the three-division display mode. The display layout is, for example, a layout obtained by, for example, dividing the display area into two, upper and lower areas and further dividing the lower half display area into left and right display areas. For the sake of simplicity, the left display area of the lower half display areas will be referred to as the first display area. The right display area of the lower half display areas will be referred to as as the second display area. The upper half display area will be referred to as the third display area. Note that the display layout (the three divided display areas) to be used is not limited to that described above. That is, it is possible to arbitrarily set a manner (display layout) of dividing the display area via, for example, the input unit 37. In addition, a display layout may be arbitrarily set in advance.

The image generation unit 29 generates a superimposed image (to be referred to as the first superimposed image hereinafter) by superimposing the first dose distribution and the first irradiation field on the patient model, with the first focal point being a viewpoint and the first direction being a line-of-sight direction. Note that the position of the first support mechanism 9 relative to the top 24 may be superimposed on the first superimposed image.

The image generation unit 29 generates a superimposed image (to be referred to as the second superimposed image hereinafter) by superimposing the second dose distribution and the second irradiation field on the patient model, with the second focal point being a viewpoint and the second direction being a line-of-sight direction. Note that the position of the second support mechanism 19 relative to the top 24 may be superimposed on the second superimposed image.

The image generation unit 29 also generates a superimposed image (to be referred to as the third superimposed image hereinafter) by superimposing the first and second dose distributions and the first and second irradiation fields on the patient model, with a predetermined position being a viewpoint and a predetermined direction being a line-of-sight direction.

The display unit 41 displays the first to third superimposed images in the first to third display areas, respectively. More specifically, the display unit 41 displays the first superimposed image in the first display area. The display unit 41 displays the second superimposed image in the second display area. The display unit 41 displays the third superimposed image in the third display area.

FIG. 9 is a view showing an example of displaying the first to third superimposed images in the first to third display areas, respectively. As shown in FIG. 9, the position of the first support mechanism 9 relative to the top 24 and the first superimposed image are displayed in the first display area. In addition, as shown in FIG. 9, the position of the second support mechanism 19 relative to the top 24 and the second superimposed image are displayed in the second display area. As shown in FIG. 9, the third superimposed image is displayed in the third display area.

(Dose Distribution Display Function)

The dose distribution display function is a function of displaying three superimposed images with different viewpoints and line-of-sight directions in three display areas, respectively. Processing (to be referred to as dose distribution display processing hereinafter) concerning the dose distribution display function will be described below.

Figure 10:
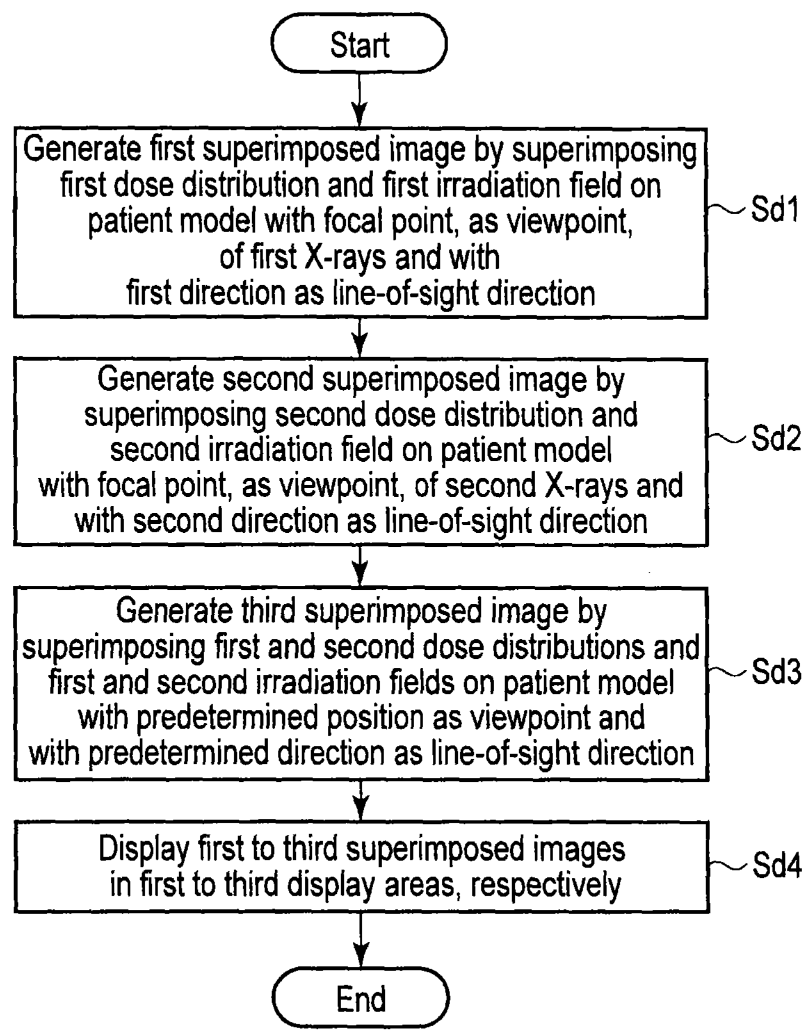
FIG. 10 is a flowchart showing an example of a procedure for dose distribution display processing according to the third modification of this embodiment.
Figure 11:
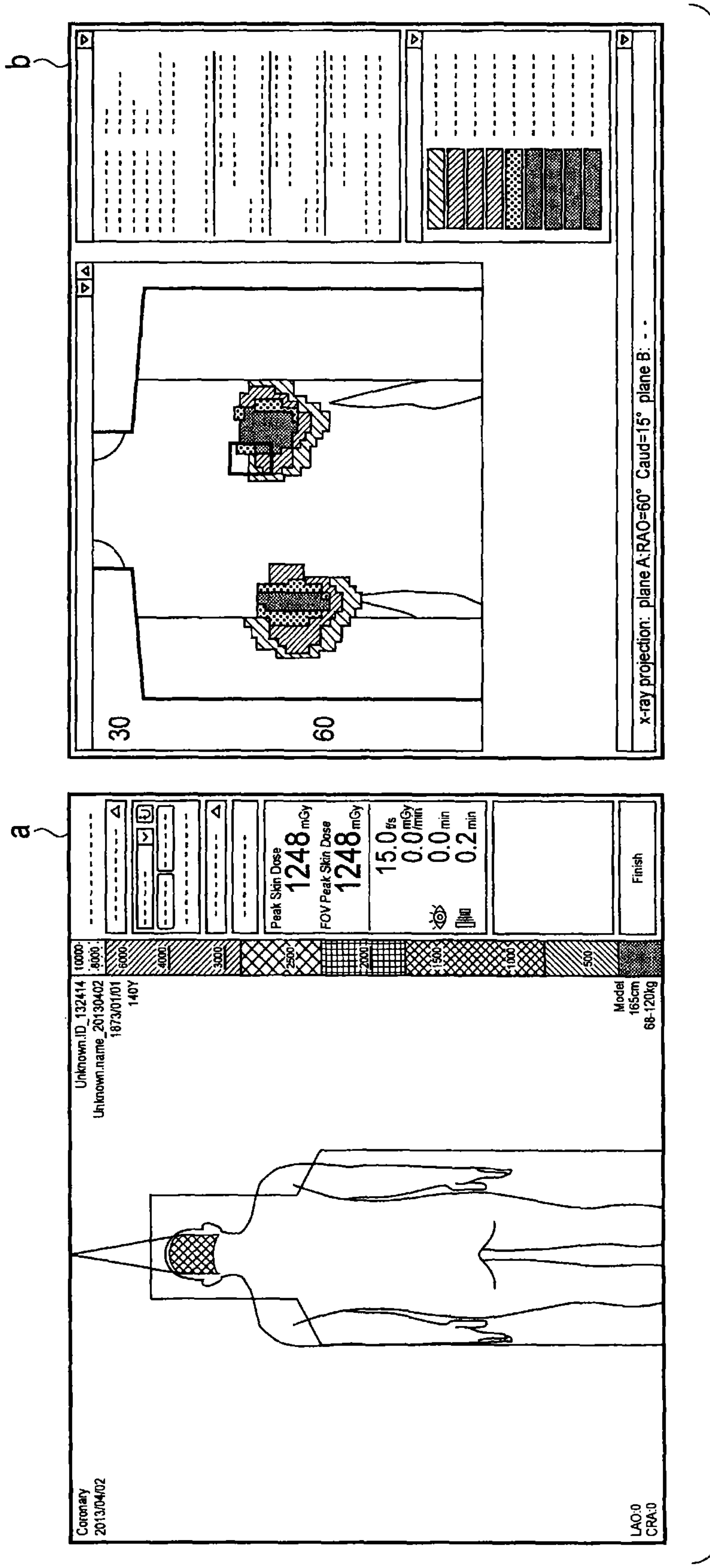
FIG. 11 shows an example of a dose distribution according to the related art.

FIG. 10 is a flowchart showing an example of a procedure for dose distribution display processing. Note that the flowchart of FIG. 10 may be executed following, for example, step Sa4 in the flowchart of FIG. 4.

The first superimposed image is generated by superimposing the first dose distribution and the first irradiation field on the patient model, with the focal point of the first X-rays being a viewpoint and the first direction being a line-of-sight direction (step Sd1). The second superimposed image is generated by superimposing the second dose distribution and the second irradiation field on the patient model, with the focal point of the second X-rays being a viewpoint and the second direction being a line-of-sight direction (step Sd2). The third superimposed image is generated by superimposing the first and second dose distributions and the first and second irradiation fields on the patient model, with a predetermined position being a viewpoint and a predetermined direction being a line-of-sight direction (step Sd3). The first to third superimposed images are respectively displayed in the first to third display areas (step Sd4).

The following effects can be obtained by the above arrangement.

The X-ray diagnostic apparatus 1 according to this embodiment can display, in different display areas, dose distributions in the first and second irradiation fields respectively corresponding to the irradiation direction of the first X-rays (first direction) and the irradiation direction of the second X-rays (second direction). That is, the X-ray diagnostic apparatus 1 according to the embodiment can display the first dose distribution corresponding to the first irradiation field and the second dose distribution corresponding to the second irradiation field as the first display with the display area being partitioned. In addition, the X-ray diagnostic apparatus 1 according to the embodiment can display at least one of the first and second dose distributions upon switching from the first display in accordance with the position states of the C-arm 91 and the Ω-arm 191 (information indicating whether they are arranged at the retracting position) or the operation states of the first X-ray tube 5 and the second X-ray tube 15 (information indicating whether X-rays are generated).

In addition, according to the first modification of this embodiment, when dose distributions are display on one screen, that is, in the second display, it is possible to selectively switch and display a dose distribution on the side where the object P is irradiated with X-rays or a dose distribution exhibiting a larger irradiation dose per unit time.

In addition, according to the second modification of this embodiment, when dose distributions are display on one screen, that is, in the second display, it is possible to switch a dose distribution exhibiting a smaller irradiation dose upon irradiation of X-rays, after being displayed in a predetermined time interval, to a dose distribution exhibiting a larger irradiation dose and display it. The X-ray diagnostic apparatus 1 according to the second modification can also switch and display a dose distribution exhibiting a smaller irradiation dose and a dose distribution exhibiting a larger irradiation dose at predetermined time intervals.

Furthermore, according to the third modification of this embodiment, it is possible to divide one display area (one screen) into three display areas and respectively display the first to third superimposed images in the three display areas. This allows the operator to check the first dose distribution concerning the first irradiation field, the second dose distribution concerning the second irradiation field, and a dose distribution viewed from below the object P without necessity to switch screens.

As has been described above, the operator of the X-ray diagnostic apparatus 1 according to this embodiment can simultaneous check dose distributions in two irradiation fields. In addition, it is possible to switch dose distributions to be displayed in accordance with the position states of the first support mechanism 9 and the second support mechanism 19, the operation states of the first X-ray tube 5 and the second X-ray tube 15, and integrated irradiation doses. In addition, it is possible to display, on one screen, the first dose distribution viewed from the first direction in the first display area, together with the first irradiation field, the second dose distribution viewed from the second direction in the second display area, together with the second irradiation field, and the first and second dose distributions viewed from a predetermined direction in the third area, together with the first and second irradiation fields. As has been described above, the X-ray diagnostic apparatus 1 according to the embodiment allows the operator to grasp an irradiation range, irradiation field, and dose distribution corresponding to each plane of a biplane system without necessity to perform any cumbersome operation.

Note that the X-ray diagnostic apparatus 1 according to this embodiment is not limited to the biplane structure constituted by the C-arm 91 and the Ω-arm 191. The X-ray diagnostic apparatus 1 according to the embodiment may be configured such that, for example, the first X-ray tube 5, the first X-ray detector 7, the second X-ray tube 15, and the second X-ray detector 17 are supported by a plurality of arms (e.g., robot arms) so as to be movable in arbitrary directions. In this case, for example, the first support mechanism 9 has the first arm which supports the first X-ray tube 5 and the second arm which supports the first X-ray detector 7. In addition, the second support mechanism 19 has the third arm which supports the second X-ray tube 15 and the fourth arm which supports the second X-ray detector 17.

In addition, each function according to this embodiment and these modifications can be implemented by installing programs for executing dose distribution switching processing and dose distribution display processing in a computer such as a workstation and expanding them in the memory. In this case, the programs which can cause the computer to execute this method can be distributed by being stored in storage media such as magnetic disks (floppy® disks, hard disks, and the like), optical disks (CD-ROMs, DVDs, and the like), and semiconductor memories.

While certain embodiments have been described, these embodiments have been presented by way of example only, and are not intended to limit the scope of the inventions. Indeed, the novel embodiments described herein may be embodied in a variety of other forms; furthermore, various omissions, substitutions and changes in the form of the embodiments described herein may be made without departing from the spirit of the inventions. The accompanying claims and their equivalents are intended to cover such forms or modifications as would fall within the scope and spirit of the inventions.

The invention claimed is:

1. An X-ray diagnostic apparatus, comprising:
- a first support mechanism that supports a first X-ray tube which irradiates an object with first X-rays along a first direction;
- a second support mechanism that supports a second X-ray tube which irradiates the object with second X-rays along a second direction different from the first direction;
- processing circuitry that
- generates a first dose distribution concerning the first X-rays;
- generates a second dose distribution concerning the second X-rays; and
- specifies position states of the first support mechanism and of the second support mechanism and operation states of the first X-ray tube and of the second X-ray tube; and
- a display that simultaneously displays, with at least two different viewpoints in accordance with the position states and the operation states, a model on which the first dose distribution and the second dose distribution are superimposed.

2. The apparatus according to claim 1, wherein the display displays the model with a focal point, as a viewpoint, of the first X-rays at the first X-ray tube and with the first direction as a line-of-sight direction.

3. The apparatus according to claim 1, wherein the display alternately displays a first display which displays the first dose distribution and the second dose distribution in different display areas and a second display which displays at least one of the first dose distribution and the second dose distribution in one display area.

4. The apparatus according to claim 1, wherein
- the first support mechanism further supports a first dosimeter which measures a first X-ray dose concerning the first X-rays,
- the second support further supports a second dosimeter which measures a second X-ray dose concerning the second X-rays, and
- the processing circuitry generates the first dose distribution based on the first X-ray dose and generates the second dose distribution based on the second X-ray dose.

5. The apparatus according to claim 1, wherein the processing circuitry
- generates the first dose distribution based on a first X-ray condition concerning the first X-rays and an X-ray dose measured in advance, and
- generates the second dose distribution based on a second X-ray condition concerning the second X-rays and the X-ray dose.

6. The apparatus according to claim 1, wherein the processing circuitry further
- specifies, as the position state, whether the first support mechanism and the second support mechanism are located at a retracting position, and
- specifies, as the operation state, whether the first X-ray tube and the second X-ray tube are operating.

7. The apparatus according to claim 3, wherein the display further
- displays, in the first display, the first dose distribution with the focal point, as the viewpoint, of the first X-rays at the first X-ray tube and the first direction as a line-of-sight direction, and
- displays, in the first display, the second dose distribution with a focal point, as a viewpoint, of the second X-rays at the second X-ray tube and with the second direction as a line-of-sight direction.

8. The apparatus according to claim 3, further comprising a top on which the object is placed,
- wherein the display displays at least one of the first dose distribution and the second dose distribution in the second display with a predetermined position, as a viewpoint, spaced apart from the top and with a predetermined direction, as a line-of-sight direction, from the predetermined position to a surface of the object.

9. The apparatus according to claim 3, wherein the processing circuitry specifies the operation state in the second display, and
- the display displays a dose distribution concerning an X-ray tube corresponding to the specified operation state in the second display.

10. The apparatus according to claim 3, wherein the processing circuitry specifies the dose distribution exhibiting a large irradiation dose with respect to the object based on the first dose distribution and the second dose distribution, and
- the display displays the specified dose distribution in the second display.

11. The apparatus according to claim 3, wherein the processing circuitry displays an ascending order of integrated irradiation doses of the object with respect to the first dose distribution and the second dose distribution based on the first dose distribution and the second dose distribution, and
- the display sequentially displays the first dose distribution and the second dose distribution in the second display at predetermined time intervals in accordance with the specified ascending order.

12. The apparatus according to claim 11, wherein the display sequentially and repeatedly displays the first dose distribution and the second dose distribution in the second display at predetermined time intervals in accordance with the specified ascending order over a predetermined count.

13. The apparatus according to claim 1, further comprising a top on which the object is placed,
- wherein the display
- displays the first dose distribution in a first display area with a focal point, as a viewpoint, of the first X-rays and with the first direction as a line-of-sight direction,
- displays the second dose distribution in a second display area different from the first display area with a focal point, as a viewpoint, of the second X-rays and with the second direction as a line-of-sight direction, and
- displays at least one of the first dose distribution and the second dose distribution in a third display area different from the first display area and the second display area with a predetermined position, as a viewpoint, spaced apart from the top and with a predetermined direction, as a line-of-sight direction, from the predetermined position to a surface of the object.

14. A dose distribution display method comprising:

storing a position of a first support mechanism configured to support a first X-ray tube configured to irradiate an object with first X-rays along a first direction, storing a position of a second support mechanism configured to support a second X-ray tube configured to irradiate the object with second X-rays along a second direction different from the first direction;

generating a first dose distribution concerning the first X-rays and a second dose distribution concerning the second X-rays;

specifying position states of the first support mechanism and of the second support mechanism and operation states of the first X-ray tube and of the second X-ray tube; and simultaneously displaying a model, with at least two different viewpoints in accordance with the position states and the operation states, on which the first dose distribution and the second dose distribution are superimposed.

* * * * *